United States Patent

Andres et al.

Patent Number: 5,281,725
Date of Patent: Jan. 25, 1994

[54] DERIVATIVES OF 2,2-DIHALOGENOBENZO[1,3]DIOXOLES SUBSTITUTED IN THE 4-POSITION, PROCESSES FOR THEIR PREPARATION AND THEIR USE

[75] Inventors: Peter Andres, Leichlingen; Albrecht Marhold, Leverkusen, both of Fed. Rep. of Germany

[73] Assignee: Bayer Aktiengesellschaft, Leverkusen, Fed. Rep. of Germany

[21] Appl. No.: 952,036

[22] Filed: Sep. 28, 1992

[30] Foreign Application Priority Data

Oct. 7, 1991 [DE] Fed. Rep. of Germany ....... 4133157

[51] Int. Cl.⁵ ............................................. C07D 317/46
[52] U.S. Cl. .................................... 549/439; 549/434
[58] Field of Search ............................... 549/439, 434

[56] References Cited

U.S. PATENT DOCUMENTS 4,722,935 2/1988 Ehrenfreund ........................ 549/439
4,886,816 12/1989 Franckowiak et al. ............. 546/276

FOREIGN PATENT DOCUMENTS 0041131 4/1979 European Pat. Off. .
3642256 12/1986 Fed. Rep. of Germany .
2200112A 7/1988 United Kingdom .

OTHER PUBLICATIONS

Ioannis M. Takis, *Journal of Heterocyclic Chemistry*, Apr.–May, 1991, pp. 625–634.

*Primary Examiner*—Nicky Chan
*Attorney, Agent, or Firm*—Sprung Horn Kramer & Woods

[57] ABSTRACT

New 2,2-dihalogeno-benzo[1,3]dioxoles substituted in the 4-position, of the general formula (I)

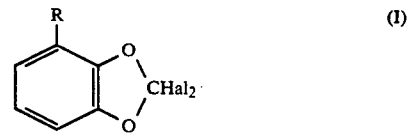

in which
R represents fluorine, chlorine, bromine or nitro and
Hal represents chlorine or fluorine, and their use as starting substances for the synthesis of highly active compounds, for example in the field of plant protection and pharmaceuticals.

The compounds of the formula (I) can be prepared by analogous processes, for example by chlorination from corresponding benzo[1,3]dioxoles substituted in the 4-position, and these substances according to the invention can be further reacted with hydrogen fluoride to give substances to which the invention likewise relates.

3 Claims, No Drawings

DERIVATIVES OF 2,2-DIHALOGENOBENZO[1,3]DIOXOLES SUBSTITUTED IN THE 4-POSITION, PROCESSES FOR THEIR PREPARATION AND THEIR USE

The present invention relates to new derivatives of 2,2-dihalogenobenzo[1,3]dioxoles which are substituted in the 4-position, processes for their preparation and their use as starting materials for the preparation of highly active biocides, such as, for example, anilino-benzo[1,3]dioxoles.

It is already known that certain anilino-benzo[1,3]-dioxoles having a biocidal action, such as, for example, 2,2-difluoro-4-(2,4-dinitro-6-trifluoromethylanilino)-benzo[1,3]dioxole, are obtained when 4-carboxybenzo[1,3]dioxole is reacted with phosphorus pentachloride to give 2,2-dichloro-benzo[1,3]dioxolo-4-carbonyl chloride, this is converted into the 2,2-difluoro-4-carbonyl fluoride derivative with antimony trifluoride, the 4-carbamide derivative is obtained therefrom with ammonia and is converted with elemental bromine and alkali metal hydroxide into the 4-amino compound, which then gives the highly active compound with the corresponding chlorobenzene derivative in the presence of lithium hydroxide and dimethyl sulphoxide (compare EP 198,797).

The new 2,2-dihalogeno-benzo[1,3]dioxoles substituted in the 4-position, of the general formula (I)

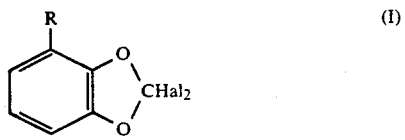

in which
R represents fluorine, chlorine, bromine or nitro and
Hal represents chlorine or fluorine,
have now been found.

The compounds are, specifically, the following compounds:

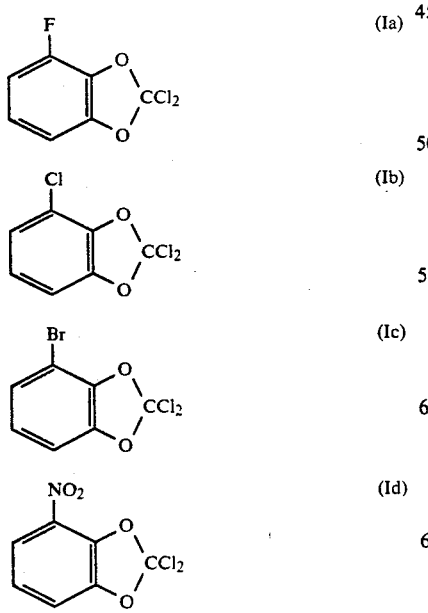

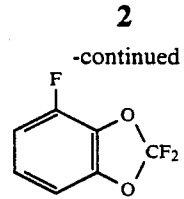

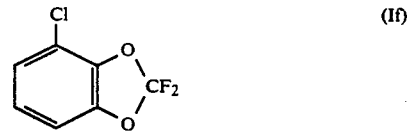

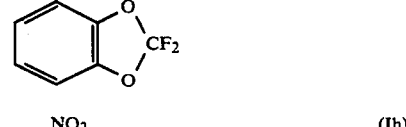

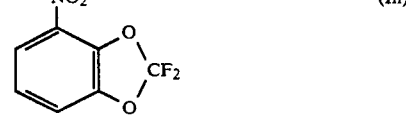

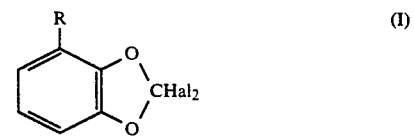

It has furthermore been found that the 2,2-dihalogenobenzo[1,3]dioxoles substituted in the 4-position, of the general formula (I)

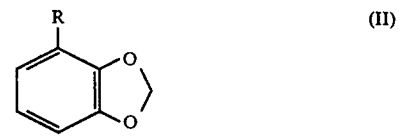

in which R represents fluorine, chlorine, bromine or nitro, are obtained by a process in which, in the case where Hal represents chlorine, a) benzo[1,3]dioxoles substituted in the 4-position, of the general formula (II)

in which R has the abovementioned meaning, are reacted with corresponding chlorinating agents, if appropriate in the presence of a free radical initiator or high-energy light, and if appropriate in the presence of a solvent, at temperatures between 0° C. and 200° C. to give the compounds of the formula (Ia) to (Id), or, in the case where Hal represents fluorine, b) 2,2-dichloro derivatives substituted in the 4-position, of the formulae (Ia) to (Id), are reacted with hydrogen fluoride, if appropriate in the presence of a solvent, at temperatures of between −20° C. and +80° C. to give the compounds of the formulae (Ic) to (Ih).

The 2,2-dihalogeno-benzo[1,3]dioxoles according to the invention, which are substituted in the 4-position, are defined by formula (I) or the formulae (Ia) to (Ih).

If 4-fluorobenzo[1,3]-dioxole and phosphorus pentachloride are used as starting materials in process variant a), the course of the reaction can be represented by the following equation:

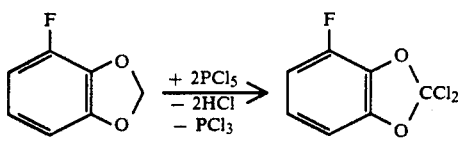

If 2,2-dichloro-4-fluoro-benzo[1,3]dioxole and hydrogen fluoride are used as starting materials in process variant b), the course of the reaction can be represented by the following equation:

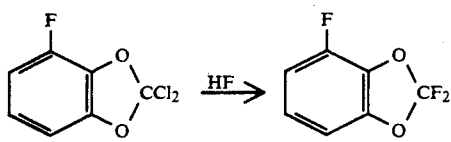

The benzo[1,3]dioxoles substituted by halogen or nitro in the 4-position, of the formula (II), which are required as starting substances in process a) according to the invention are known (compare EP 82 681, DE 3 742 515 and J. Heterocycl. Chem. 28 (1991) 625.)

All the customary chlorinating agents are possible for carrying out variant a) of the chlorination. These include, for example, phosphorus pentachloride, phosphorus trichloride and chlorine, elemental chlorine and furthermore sulphuryl chloride.

Phosphorus pentachloride is preferably employed.

If elemental chlorine or sulphuryl chloride is used, the reaction is preferably carried out in the presence of a free radical initiator or or in the presence of UV light.

The free radical initiator is employed in an amount of 0.0001 to 0.05 mol per mol of the compound of the formula (II).

Free radical initiators which can be employed are, for example, AIBN, dibenzoyl peroxide, succinyl peroxide, di-t-butyl peroxide and diacetyl peroxide.

Variant a) can be carried out in the presence of a solvent. Possible solvents are chlorinated hydrocarbons, such as, for example, carbon tetrachloride, methylene chloride and the like.

The reaction is preferably carried out without a solvent if phosphorus pentachloride and phosphorus trichloride/chlorine are used, while it is preferably carried out in a solvent, preferably in carbon tetrachloride, if chlorine or sulphuryl chloride is used.

The ratio of the chlorinating agent to the compounds of the formula (II) can be varied within a substantial range, and is 2:1 to 4:1, preferably 2.2:1.

The temperature in variant a) can be varied within a substantial range. The reaction is in general carried out at between 0° C. and 200° C.

The reaction is preferably carried out at between 60° C. and 100° C. if elemental chlorine or sulphuryl chloride is employed as the chlorinating agent with free radical initiators.

In the case of elemental chlorine or sulphuryl chloride with UV imitation, the reaction is preferably carried out at between 10° C. and 40° C.

In the case of phosphorus pentachloride or phosphorus trichloride and chlorine, the reaction is preferably carried out at between 80° C. and 180° C., in particular between 90° C. and 160° C.

The reaction time can also vary. The reaction is carried out up to the end of the evolution of hydrogen chloride and the mixture is then worked up in the customary manner, for example if appropriate by stripping off the solvent and fractional distillation in vacuo.

Variant b) employs, as starting materials, the dichloro compounds which are obtained under variant a), are defined by formula (I) or the formulae (Ia) to (Id), are new and likewise form part of the invention.

For carrying out variant b), hydrogen fluoride is employed for replacement of the chlorine atoms in the 2-position by fluorine atoms.

If appropriate, variant b) can be carried out in a solvent. Suitable solvents are alkylated or chlorinated aromatics, preferably toluene or chlorobenzene.

The weight ratio of hydrogen fluoride to toluene, if this is employed as the solvent, varies between 1:2 and 2:1, and is preferably 1:1.

The ratio of hydrogen fluoride to the dichloro compounds employed varies between 2:1 and 20:1 and is preferably 10:1.

The temperature in variant b) can vary within a substantial range. The reaction is in general carried out at temperatures of between −20° C. and +80° C., preferably between −10° C. and 60° C. and particularly preferably between −10° C. and 30° C.

The reaction time varies; the reaction is carried out up to the end of the evolution of hydrogen chloride. Working up is carried out by customary methods, for example by stripping off the excess hydrogen fluoride and subsequent distillation or phase separation with subsequent distillation of the organic phase, if appropriate after washing the organic phase with water and drying it, or with the addition of alkali metal fluorides.

The compounds of the formula (I) are valuable starting substances for the preparation of highly active biocides. The nitro compound can thus be reduced to the amino compound, which is then reacted with a chlorobenzene derivative to give the highly active compound 2,2-difluoro-4-(2,4-dinitro-6-trifluoromethyl-anilino)-benzo[1,3]dioxole, which is used in agents for combating pests, preferably phytopathogenic fungi or bacteria, and furthermore insects and acarids (compare EP 198 797).

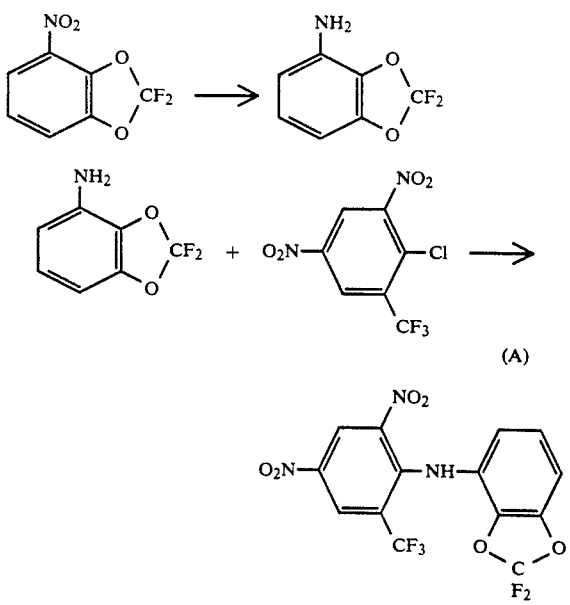

This known compound of the formula (A) has a very advantageous biocidal action spectrum, which is particularly satisfactory for requirements in practice, against fungi, bacteria, insects and representatives of the order Acarina, in particular against phytopathogenic fungi and bacteria. It has very advantageous curative, systemic and in particular preventive properties, and can be employed for protecting numerous crop plants. Using the active compound of the formula (A), the pests which occur on plants or on parts of plants (fruit, blossom, foliage, stem, tubers, roots) of various crop plants can be suppressed or destroyed, parts of plants which additionally grow later also remaining protected from phytopathogenic microorganisms and insects. Adarina can furthermore be combated successfully with the active compound of the formula I.

As a microbicide, the active compound of the formula (A) is active, for example, against the phytopathogenic fungi belonging to the following classes: *Fungi imperfecti* (for example Botrytis, Helminthosporium, Fusarium, Septoria, Cercospora and Alternaria); Basidiomycetes (for example the genera Hemileia, Thizocotonia and Puccinia); and against the Oomycetes belonging to the class of Phycomycetes (for example *Plasmopara viticola*); and in particular against the class of Ascomycetes (for example Venturia, Podospharea, Erysiphe, Monilinia and Uncinula). The compound of the formula (A) moreover becomes systemic. It can furthermore be employed as a dressing agent for the treatment of seed (fruit, tubers, grains) and plant seedlings to provide protection from fungal infections nd against phytopathogenic fungi which occur in the soil.

As an insecticide, the compound of the formula (A) can also be employed for combating insects of the order: Lepidoptera, Coleoptera, Homoptera, Heteroptera, Diptera, Thysanoptera, Orthoptera, Blattaria, Anoplura, Siphonaptera, Mallophaga, Thysanura, Isoptera, Psocoptera and Hymenoptera.

The compound of the formula (A) is moreover suitable for combating representatives of the order Acarina, for example of the families Ioxididae, Argasidae, Tetranychidae and Dermanyssidae. The compound of the formula (A) can be employed successfully for combating phytopathogenic mites, for example of the family Tetranychidae and Phytoptipalpidae (spider mites), Tarsonemidae (tarsonemids) and Eriophydiae (gall mites).

As well as having an action against mosquitoes and flies, such as, for example, *Aedes aegypti* and *Musca domestica*, the compound of the formula (A) can also be employed for combating phytopathogenic eating insects in ornamental and crop plants, in particular in cotton crops (for example against *Spodoptera littoralis* and *Heliothis virescens*), and in cereal, fruit and vegetable crops (for example against *Laspeyresia pomonella*, *Leptinotarsa decemlineata* and *Epilachna varivestis*). The compound of the formula (A) is also distinguished by a good action against larval stages of development and nymphs, in particular of insects which cause damage by eating.

The compound of the formula (A) can furthermore be used for combating ectoparasitic insects and acarids on domestic and stock animals, for example by treatment of the animal, stall and pasture.

The nitro compound of the formula (I) or of the formula (Ih) according to the invention can be employed directly as a precursor, for example for the synthesis of the compound of the formula (A). The advantage is that the 2,2-difluoro derivatives are obtained in only 2 reaction steps by a uniform process starting from known compounds, without side reactions and without metal fluorides which pollute the environment having to be employed, which is the case in the known process. That process is moreover a four-stage reaction, and the present process has only 3 stages, since reduction of the nitro group to the amino group is also included.

The 4-bromo-2,2-difluorobenzo(1,3)dioxole according to the invention can be used as the starting material, for example, for the synthesis of 3-(2,2-difluorobenzo[1,3]-dioxol-4-yl)-4-cyanopryrrole. This compound, its preparation and use in microbicidal agents are described in EP 206 999. The compound is prepared from the corresponding cinnamic acid nitrile with tosmic, and the cinnamic acid nitrile is reacted from the corresponding amine, via the diazonium salt, to give the 1-chloro-1-cyanoethyl derivative, which then gives the cinnamic acid nitrile.

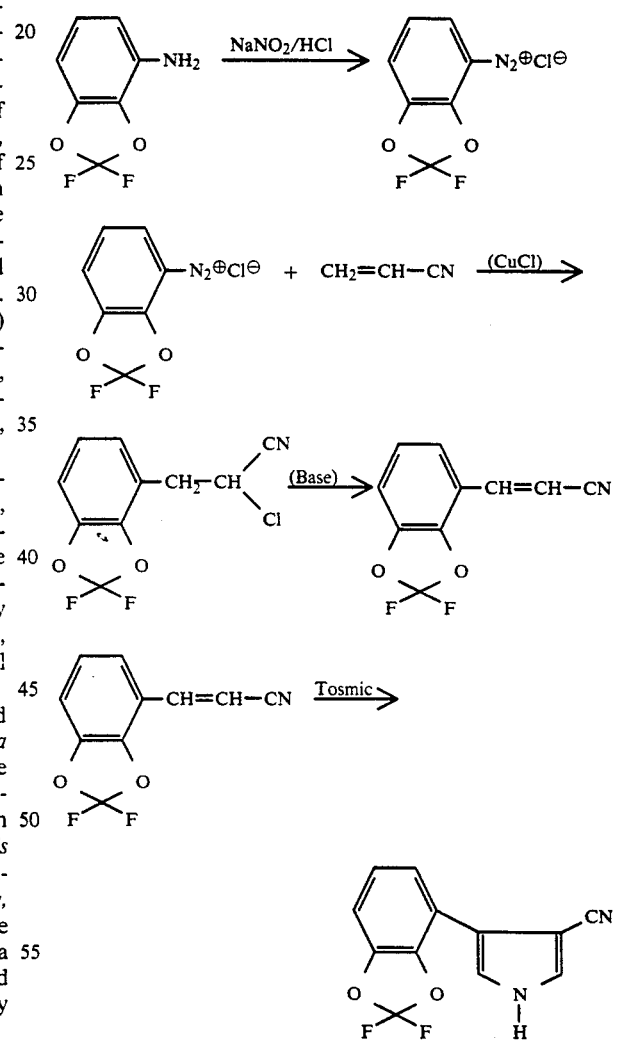

Tosmic = p-toluenesulphonylmethyl isocyanide (compare EP 206 999).

The cinnamic acid nitrile can be synthesised in a simple manner in excellent yields (97% of theory) from the 4-bromo-2,2-difluorobenzo(1,3)dioxole according to the invention with acrylonitrile in the presence of palladium acetate in a one-stage reaction (compare the preparation section). The reaction to give the end product is carried out as described above.

Several stages are saved in the reaction, the palladium acetate employed can be recovered and the waste water is therefore not polluted as is the case, for example, when copper chloride is employed in stage 2 of the known process.

Generally, it can thus be said that the new products are starting substances for the synthesis of the most diverse highly active compounds in plant protection or in the pharmaceuticals sector. Since there is always a need for new precursors which are easy to prepare, they are to be regarded as an advance.

PREPARATION EXAMPLES

Example 1

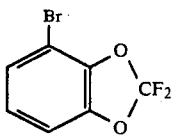

54 g (0.2 mol) of 4-bromo-2,2-dichloro-benzo[1,3]dioxole are stirred vigorously with 50 g of anhydrous hydrogen fluoride in 75 ml of toluene at 0° C. for 3 hours. The reaction mixture is then poured onto ice, neutralised with an excess of potassium hydroxide and extracted with ether, the extract is washed with 5% strength sodium bicarbonate solution and water, dried over magnesium sulphate and concentrated and the product is distilled. 33.6 g (71% of theory) of 4-bromo-2,2-difluoro-benzo[1,3]dioxole having a boiling point of 67° C./16 mbar are obtained.

EXAMPLE 2

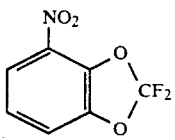

108 g (91% pure, 416 mmol) of 4-nitro-2,2-dichlorobenzo[1,3]dioxole, 100 ml of toluene and 100 g of anhydrous hydrogen fluoride are stirred vigorously at 0° C. until, according to GC*, most of the starting material has reacted.

*(gas chromatography)

Most of the hydrogen fluoride is then stripped off in vacuo, the residue is poured onto ice and the mixture is neutralised with an excess of potassium hydroxide and extracted with ether. The extract is washed with 5% strength sodium bicarbonate solution, dried over magnesium sulphate and concentrated and the product is distilled in vacuo.

32 g (38% of theory) of 4-nitro-2,2-difluoro-benzo[1,3]-dioxole of boiling point 120°-122° C./16 mbar are isolated.

EXAMPLE 3

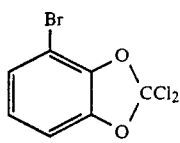

151 g (0.75 mmol) of 4-bromo-benzo[1,3]dioxole are added in portions to 312.8 g (1.5 mmol) of phosphorus pentachloride with exclusion of moisture and under a dry stream of nitrogen, and the mixture is heated at 120° C. for 3 hours. The phosphorus trichloride is distilled off and the product is distilled in vacuo. 198 g (98% of theory) of 4-bromo-2,2-dichlorobenzo[1,3]dioxole of boiling point 126°-129° C./20 mbar and melting point 49°-51° C. are obtained.

EXAMPLE 4

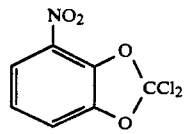

78.0 g (467 mmol) of 4-nitro-benzo[1,3]dioxole are mixed with 97.4 g (467 mmol) of phosphorus pentachloride and the mixture is heated under nitrogen until it liquefies. A further 97.4 g (467 mmol) of phosphorus pentachloride are then added and the mixture is heated at about 140° C. until the evolution of HCl gas has ended. The phosphorus trichloride formed is then distilled off.

After distillation under a high vacuum, 108 g (98% of theory) of 4-nitro-2,2-dichloro-benzo[1,3]dioxole of boiling point 120°-121° C./0.6 mbar are obtained.

The following compounds can be prepared analogously to the preparation examples mentioned:

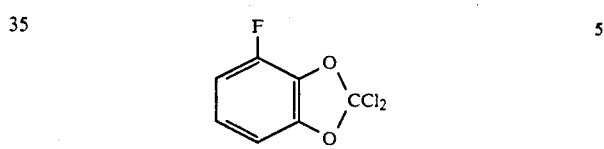 5

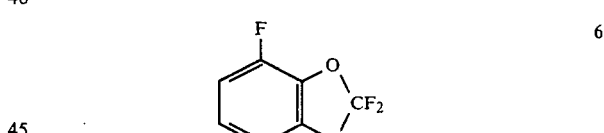 6

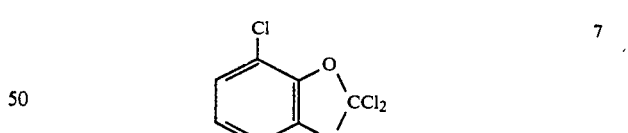 7

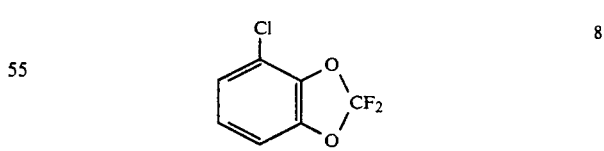 8

Further Processing Stage

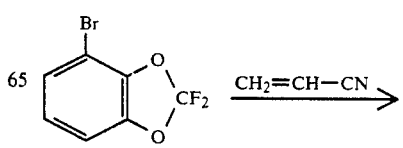

-continued

9.5 g (0.04 mol) of 4-bromo-2,2-difluoro-benzo[1,3]dioxole and 3.2 g (0.06 mol) of acrylonitrile are initially introduced into 100 ml of dimethylformamide, and 0.18 g (0.82 mmol) of palladium acetate, 8.4 g (0.10 mol) of sodium bicarbonate and 4.5 g (0.016 mol) of tetrabutylammonium chloride are added and the mixture is heated at 120° C. After a reaction time of 16 hours, a further 1.6 g (0.03 mol) of acrylonitrile, 0.09 g (0.41 mmol) of palladium acetate, 4.2 g (0.05 mol) of sodium bicarbonate and 2.25 g (0.008 mol) of tetrabutylammonium chloride are added to the reaction mixture in order to bring the reaction to completion, and the mixture is heated again at 120° C. for 16 hours. It is poured into water and extracted with ethyl acetate and the extract is washed with water and 2 normal hydrochloric acid, dried, and freed from the solvent in vacuo.

8.2 g (97% of theory) of 2,3-difluoromethylenedioxycinnamic acid nitrile are obtained as a brown oil.

Further processing is carried out as described in the literature.

We claim:

1. A 2,2-dihalogenobenzo(1,3)dioxole substituted in the 4-position, of the general formula

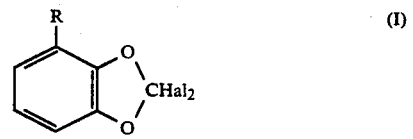

in which
R represents bromine or nitro and
Hal represents chlorine or fluorine.

2. A compound of the formula (I) according to claim 1, in which
Hal represents chlorine.

3. A compound of the formula (I) according to claim 1, in which
Hal represents fluorine.

* * * * *